(12) United States Patent
Hoshikawa et al.

(10) Patent No.: US 10,184,898 B2
(45) Date of Patent: Jan. 22, 2019

(54) DETECTION DEVICE

(71) Applicant: FUJI CORPORATION, Chiryu (JP)

(72) Inventors: Kazumi Hoshikawa, Toyohashi (JP); Kenji Shimosaka, Obu (JP)

(73) Assignee: FUJI CORPORATION, Chiryu (JP)

( * ) Notice: Subject to any disclaimer, the term of this patent is extended or adjusted under 35 U.S.C. 154(b) by 0 days.

(21) Appl. No.: 15/322,477

(22) PCT Filed: Jun. 30, 2014

(86) PCT No.: PCT/JP2014/067417
§ 371 (c)(1),
(2) Date: Dec. 28, 2016

(87) PCT Pub. No.: WO2016/001983
PCT Pub. Date: Jan. 7, 2016

(65) Prior Publication Data
US 2017/0131215 A1  May 11, 2017

(51) Int. Cl.
*H05K 13/04* (2006.01)
*G01N 21/88* (2006.01)
(Continued)

(52) U.S. Cl.
CPC ......... *G01N 21/8806* (2013.01); *G01B 11/00* (2013.01); *G01N 21/01* (2013.01);
(Continued)

(58) Field of Classification Search
CPC ............... G01N 21/8806; G01N 21/94; G01N 2201/061; G01N 2201/068; H04N 5/2256;
(Continued)

(56) References Cited

U.S. PATENT DOCUMENTS 4,793,707 A * 12/1988 Hata ................ B23P 19/00
29/721
6,640,431 B1 * 11/2003 Yoriki ............... H05K 13/0408
29/703
(Continued)

FOREIGN PATENT DOCUMENTS

JP          62-73141 A       4/1987
JP          11230717    *    2/1998 ............. G01B 11/00
(Continued)

OTHER PUBLICATIONS

Extended European Search Report dated Jan. 31, 2018 in Patent Application No. 14896703.7.
(Continued)

*Primary Examiner* — Peter D Le
*Assistant Examiner* — Howard D Brown, Jr.
(74) *Attorney, Agent, or Firm* — Oblon, McClelland, Maier & Neustadt, L.L.P.

(57) ABSTRACT

Imaging device is provided with lower lighting device, side lighting device, and camera; light is emitted to suction nozzle from below by the lower lighting device, and light is emitted onto the suction nozzle from a sideways direction by the side lighting device. Light emitted from the lower lighting device arrives at the camera via a first light path (the path between the two dotted lines); light emitted from the side lighting device arrives at the camera via a second light path (the path between the two dotted lines). Further, light emitted from the lower lighting device is blocked by light-blocking blocks so as not to arrive at the camera along the second light path.

6 Claims, 10 Drawing Sheets

(51) Int. Cl.
*G01N 21/01* (2006.01)
*H05K 13/08* (2006.01)
*G01B 11/00* (2006.01)
*G01N 21/94* (2006.01)
*G06T 7/00* (2017.01)
*H04N 5/225* (2006.01)
*H04N 7/18* (2006.01)

(52) U.S. Cl.
CPC ........... *G01N 21/94* (2013.01); *G06T 7/0004* (2013.01); *H04N 5/2256* (2013.01); *H04N 7/183* (2013.01); *H05K 13/043* (2013.01); *H05K 13/0408* (2013.01); *H05K 13/08* (2013.01); *G01N 2201/061* (2013.01); *G01N 2201/068* (2013.01)

(58) Field of Classification Search
CPC .... H04N 7/183; H05K 13/0408; H05K 13/08; H05K 13/043; H05K 13/028; G06T 7/0004; G01B 11/00; B65G 47/12; B65G 15/58; G05B 19/4189; G05B 2219/45031
See application file for complete search history.

(56) References Cited

U.S. PATENT DOCUMENTS

| | | | | |
|---|---|---|---|---|
| 8,447,566 | B2 * | 5/2013 | Maenishi | H05K 13/08 29/830 |
| 2002/0070102 | A1 * | 6/2002 | Kawada | H05K 13/0061 198/817 |
| 2002/0154491 | A1 * | 10/2002 | Suhara | H05K 13/0069 361/752 |
| 2005/0258381 | A1 * | 11/2005 | Kawase | H05K 13/0408 250/559.45 |
| 2007/0065549 | A1 * | 3/2007 | Hinderliter | A23N 17/005 426/511 |
| 2015/0282399 | A1 * | 10/2015 | Nozawa | H05K 13/028 29/740 |

FOREIGN PATENT DOCUMENTS

| | | | | |
|---|---|---|---|---|
| JP | 11230717 | A * | 2/1998 | ............. G01B 11/00 |
| JP | 11-230717 | A | 8/1999 | |
| JP | 2004349346 | | * 5/2003 | ............. H05K 13/08 |
| JP | 2004-349346 | A | 12/2004 | |
| JP | 2006-41158 | A | 2/2006 | |
| JP | 2012-4306 | A | 1/2012 | |
| WO | 2013/111550 | A1 | 8/2013 | |

OTHER PUBLICATIONS

International Search Report dated Sep. 9, 2014 in PCT/JP2014/067417 filed Jun. 30, 2014.

* cited by examiner

DETECTION DEVICE

TECHNICAL FIELD

The present application relates to a detection device that detects light emitted onto a detection target object.

BACKGROUND ART

Among detection devices that detect light emitted onto a detection target object, for example, there are items that perform inspection of the detection target object by capturing an image of the detection target object based on detected light and using image data formed from the captured image. Technology disclosed in patent literature 1 is for performing inspection of a detection target object by imaging the detection target object from two directions using two imaging devices and performing inspection based on image data formed from the images captured from the two directions. Also, because the efficiency is poor when imaging the detection target object from two directions using two imaging devices, technology disclosed in patent literature 2 is for imaging a detection target object from two directions using only one imaging device.

Patent Literature 1: JP-A-2006-41158
Patent Literature 2: JP-A-2012-4306

SUMMARY

As disclosed in patent literature 2 above, it is possible to lower costs by imaging a detection target object from two directions using one imaging device. However, in a case of imaging a detection target object from two directions using one imaging device, usually the path of light when imaging the detection target object from a first direction (hereinafter referred to as a "first light path") and the path of light when imaging the detection target object from a second direction (hereinafter referred to as a "second light path") are different, and from the light passing along each path, image data of the detection target object captured from the first direction and image data of the detection target object captured from the second direction are formed. However, there are cases in which light emitted when the detection target object is captured from the first direction enters the second light path as well as the first light path. In such a case, there is a tendency for a ghost image to appear in an image captured of the detection target object from the first direction due to light entering the second light path, meaning that appropriate inspection of the detection target object cannot be performed. The present disclosure takes account of such problems and an object thereof is to prevent the appearance of a ghost image in an image when capturing a detection target object from a first direction.

Solution to Problem

To solve the above problems, the disclosed detection device is a detection device that detects light emitted onto a detection target object, including: a first light source that emits light onto the detection target object from a first direction; a second light source that emits light onto the detection target object from a second direction; a detecting section for detecting light emitted from the first light source and light emitted from the second light source; a first guiding member that guides light emitted from the first light source to the detecting section via a first light path; a second guiding member that guides light emitted from the second light source to the detecting section via a second light path; and a light-blocking member that blocks light emitted from the first light source such that light emitted from the first light source does not arrive at the detecting section along the second light path.

Advantageous Effects of Invention

With the disclosed detection device, light is emitted onto a detection target object from a first direction by a first light source, and light is emitted onto the detection target object from a second direction by a second light source. Also, light emitted from the first light source arrives at a detecting section via a first light path, and light emitted from the second light source arrives at the detecting section via a second light path. Further, light emitted from the first light source is blocked by a light-blocking member so as not to arrive at the detecting section along the second light path. By this, the appearance of a ghost image in the image when imaging the detection target object from the first direction is prevented.

BRIEF DESCRIPTION OF DRAWINGS

FIG. 3 is a perspective view showing a nozzle management device.

DESCRIPTION OF PREFERRED EMBODIMENTS

The following describes in detail referring to the figures an example embodiment.

Configuration of Electronic Component Mounting Device

Figure 1:
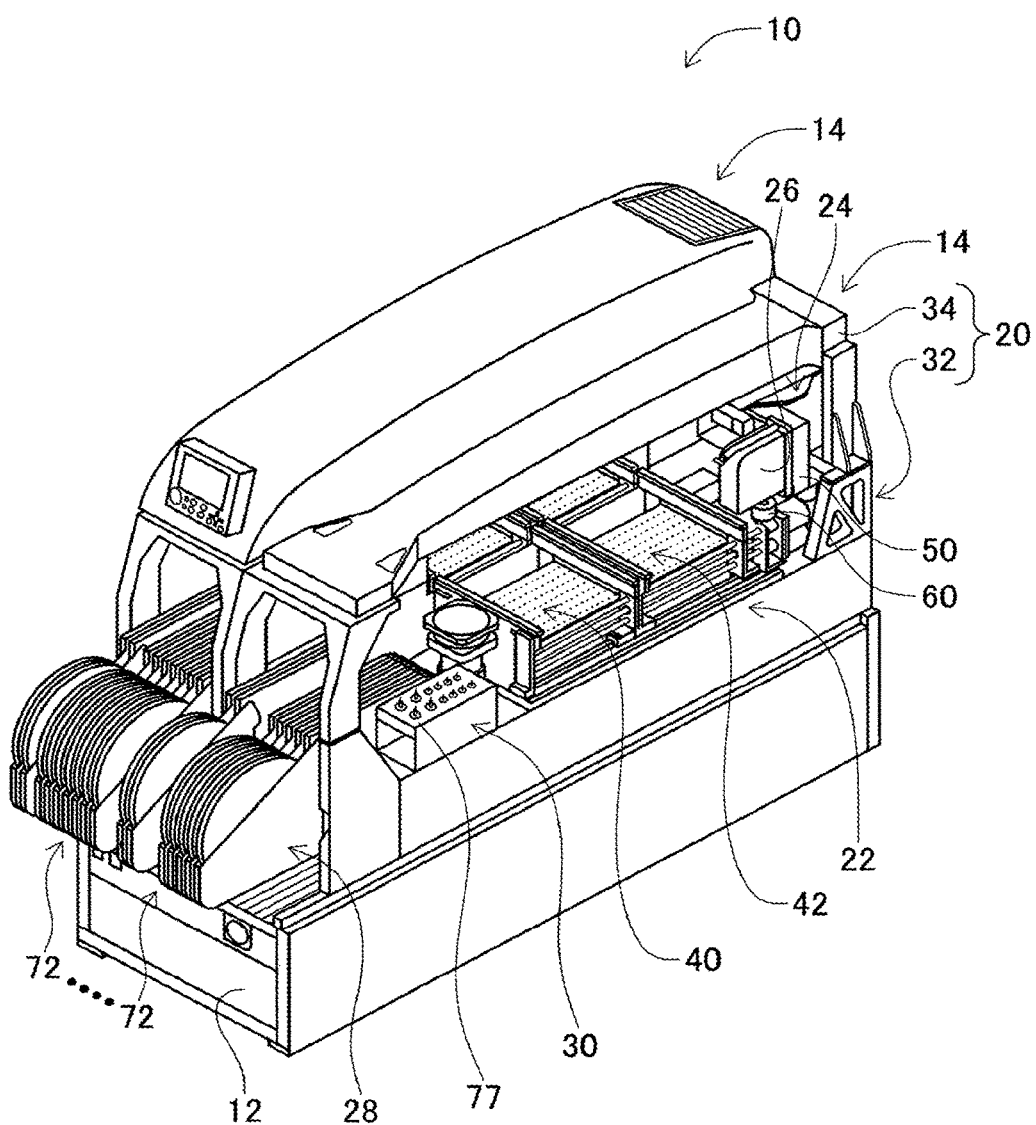
FIG. 1 is a perspective view of an electronic component mounter.

Electronic component mounting device (hereinafter in some cases abbreviated to "mounting device") 10 is shown in FIG. 1. Mounting device 10 includes one system base 12, and two electronic component mounters (hereinafter in some cases abbreviated to "mounter") 14 provided adjacently to each other on system base 12. Note that, the direction in which the mounters 14 are lined up is referred to as the X-axis direction, and the horizontal direction which is perpendicular to the X-axis direction is referred to as the Y-axis direction.

Each mounter 14 is provided mainly with mounter body 20, conveyance device 22, mounting head moving device (hereinafter in some cases abbreviated to "moving device") 24, mounting head 26, supply device 28, and nozzle station 30. Mounter body 20 is configured from frame 32 and beam 34 that is mounted on the frame 32.

Conveyance device 22 is provided with two conveyor devices 40 and 42. The two conveyor devices 40 and 42 are parallel to each other and are provided on frame 32 extending in the X-axis direction. Each of the two conveyor devices 40 and 42 conveys a circuit board held on the respective conveyor devices 40 and 42 in the X-axis direction using an electromagnetic motor (not shown). Also, the circuit board is fixedly held at a predetermined position by a board holding device (not shown).

Moving device 24 is an XY robot type moving device. Moving device 24 is provided with an electromagnetic motor (not shown) that slides a slider 50 in the X-axis direction, and an electromagnetic motor (not shown) that slides slider 50 in the Y-axis direction. Mounting head 26 is attached to slider 50, and the mounting head 26 is moved to any position on frame 32 by the operation of the two electromagnetic motors.

Figure 2:
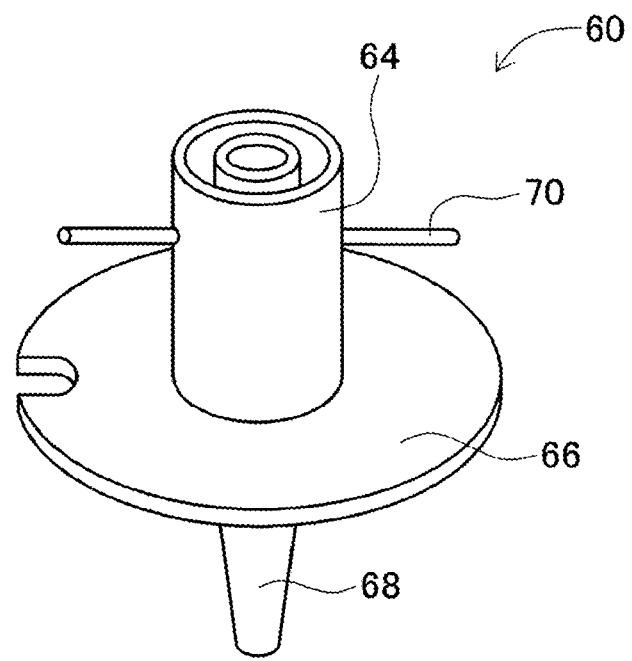

Mounting head 26 mounts electronic components on a circuit board. Suction nozzle 60 is provided on the lower end of mounting head 26. As shown in FIG. 2, suction nozzle 60 is configured from body pipe 64, flange 66, suction tube 68, and locking pin 70. Body pipe 64 is cylindrical and flange 66 is fixed to the outer surface of body pipe 64 so as to project outwards. Suction tube 68 is a thin pipe that is held on body pipe 64 movable in an axis line direction in a state extending downwards from the lower end of body pipe 64. Locking pin 70 is provided on an upper section of body pipe 64 such that locking pin 70 extends in the diameter direction of body pipe 64. Suction nozzle 60 is attached to mounting head 26 using locking pin 70 such that suction nozzle 60 is attachable/detachable with one touch. Also, a spring (not shown) is built into mounting head 26, and the spring applies elastic force to suction pipe 68 of suction nozzle 60 attached to mounting head 26. By this, suction tube 68 is biased so as extend down from the lower end of body pipe 64 by the elastic force of the spring built into mounting head 26.

Further, suction nozzle 60 is connected to a positive/negative pressure supply device (not shown) via a negative pressure air and positive pressure air passage. Each suction nozzle 60 picks up and holds an electronic component using negative pressure, and releases the held electronic component using positive pressure. Also, mounting head 26 has a nozzle raising/lowering device (not shown) that raises/lowers suction nozzle 60. Mounting head 26 changes the position of the held electronic component in a vertical direction by the nozzle raising/lowering device.

Supply device 28 is a feeder type supply device and, as shown in FIG. 1, is provided on the front end of frame 32. Supply device 28 has tape feeders 72. Tape feeders 72 house taped components in a wound state. Taped components are electronic components that have been put into tape. Tape feeders 72 deliver the taped components using an indexing device (not shown). Accordingly, feeder type supply device 28 supplies an electronic component to a supply position through the feeding delivery of the taped components.

Nozzle station 30 has nozzle tray 77 that stores multiple suction nozzles 60. Using nozzle station 30, exchange and so on is performed as necessary between suction nozzles 60 attached to mounting head 26 and suction nozzles 60 housed in nozzle tray 77. Also, nozzle tray 77 is attachable/detachable to/from nozzle station 30 such that the collection of suction nozzles 60 housed in nozzle tray 77, or the replenishment of suction nozzles 60 to nozzle tray 77, and the like, can be performed outside mounter 14.

Mounting Work by a Mounter

It is possible to perform mounting work with respect to a circuit board held in conveyance device 22 using mounting head 26 in mounter 14 with the above configuration. Specifically, based on commands of a control device (not shown) of mounter 14, a circuit board is conveyed to a work position, and the circuit board is fixedly held at that position by a board holding device. Also, based on commands of the control device, tape feeder 72 feeds taped components and supplies an electronic component to a supply position. Then, mounting head 26 moves above the supply position of the electronic component and picks up and holds the electronic component using suction nozzle 60. Continuing, mounting head 26 moves above the circuit board and mounts the held electronic component on the circuit board.

Suction Nozzle Inspection

In mounter 14, as given above, an electronic component supplied by tape feeder 72 is picked up and held by suction nozzle 60 and then mounted on the circuit board. Thus, if a problem occurs with suction nozzle 60, mounting work cannot be performed properly. Considering this, nozzle tray 77 is removed from nozzle station 30 of mounter 14, and inspection of suction nozzles 60 housed in nozzle tray 77 is performed at a nozzle management device.

Figure 3:
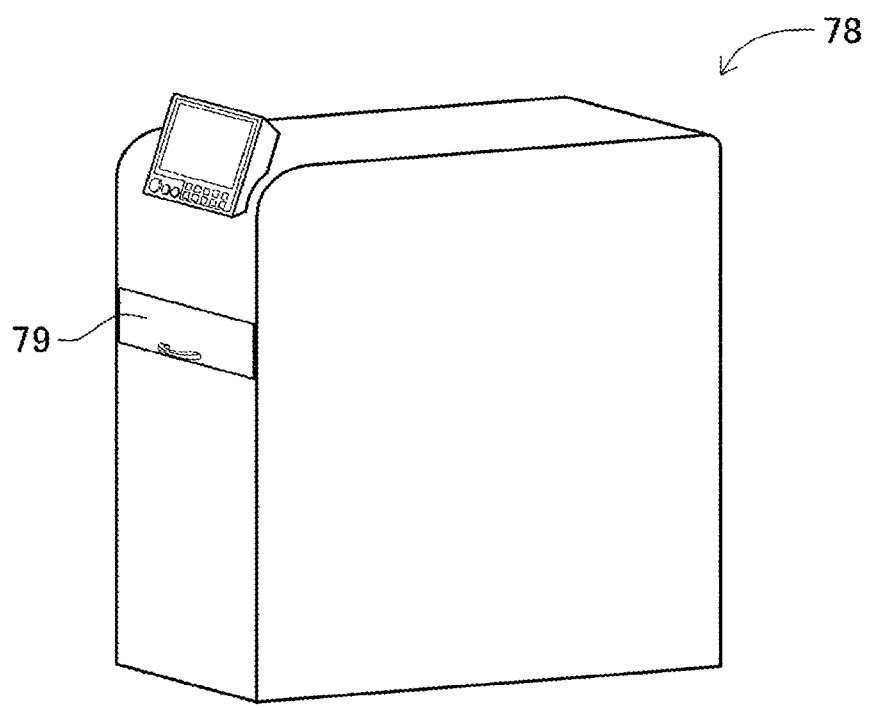
FIG. 3 is perspective view of a suction nozzle.
Figure 4:
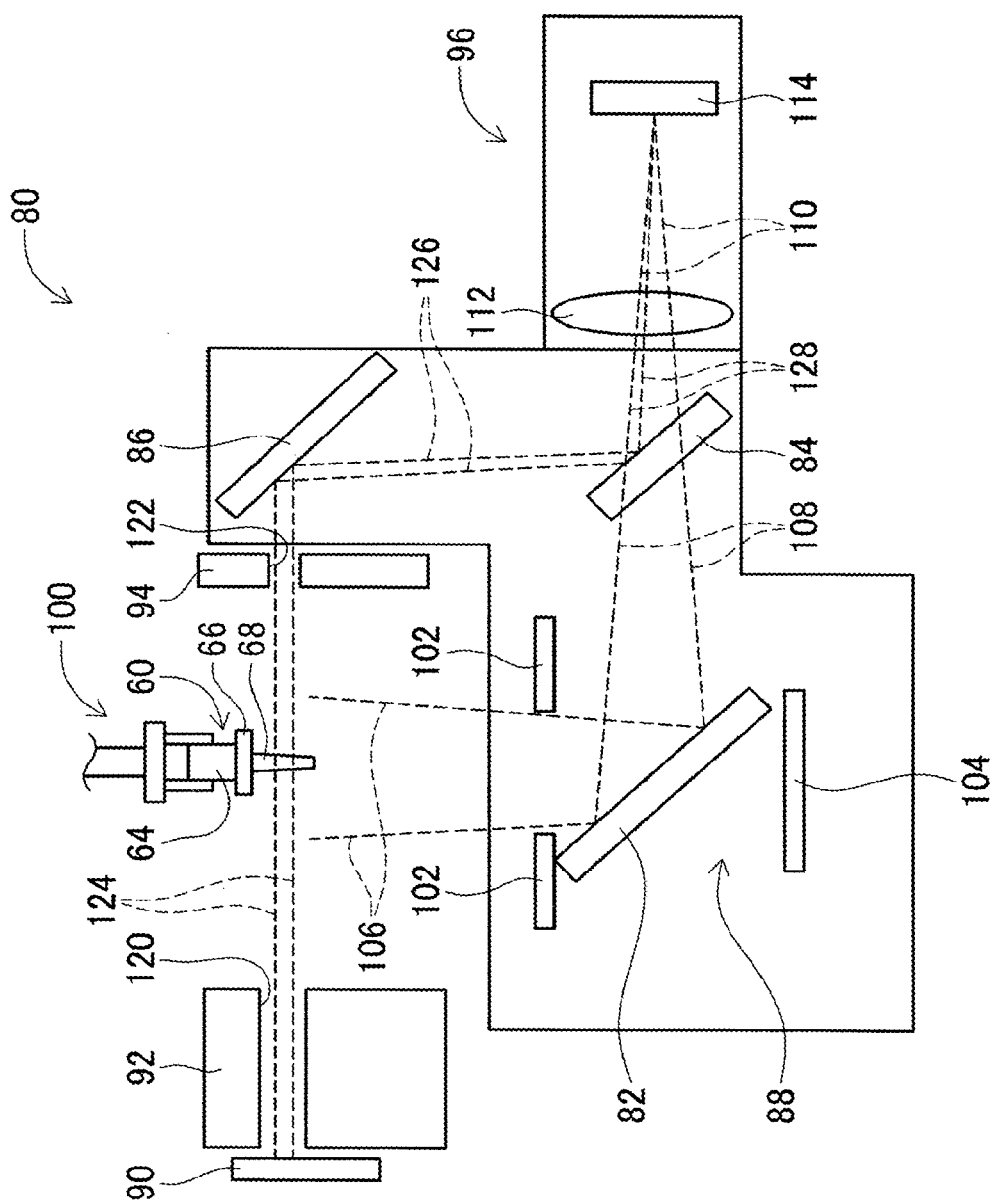
FIG. 4 is a schematic drawing showing an imaging device of the present disclosure.

In detail, as shown in FIG. 3, nozzle management device 78 is largely a rectangular cuboid and drawer 79 for storing nozzle tray 77 inside nozzle management device 78, and for removing nozzle tray 77 from nozzle management device 78, is provided on the front surface of nozzle management device 78. Suction nozzles 60 are stored inside nozzle management device 78, with management and inspection being performed inside nozzle management device 78. When inspecting suction nozzle 60, suction nozzle 60 is imaged, then, based on the image data, the state of suction tube 68 of suction nozzle 60, and the protrusion amount of nozzle pipe 64 from nozzle tube 68 is inspected. As shown in FIG. 4, imaging device 80 that performs imaging of suction nozzle 60 is provided with three reflectors 82, 84, and 86, lower lighting device 88, side lighting device 90, two light-blocking blocks 92 and 94, and camera 96.

In nozzle management device 78, suction nozzle 60 that is the inspection target is held by nozzle holding tool 100. Then, suction nozzle 60 held by nozzle holding tool 100 is imaged by imaging device 80. Among the three reflectors 82, 84, and 86, first reflector 82 is provided at a 45 degree angle below suction nozzle 60 held by nozzle holding tool 100. The reflectance of first reflector 82 is 50%, and the permeability is 50%.

Among the three reflectors 82, 84, and 86, second reflector 84 is provided to the side of first reflector 82 inclined at a 45 degree angle in the same direction as first reflector 82. The reflectance of second reflector 84 is 30%, and the permeability is 70%. Among the three reflectors 82, 84, and 86, third reflector 86 is provided above second reflector 84 inclined at a 45 degree angle in the same direction as second reflector 84. The reflectance of third reflector 86 is 100%, and permeability is 0%.

Lowering light device 88 is provided with side illumination 102 and front illumination 104. Side illumination 102 is roughly circular and is provided between first reflector 82 and suction nozzle 60 held by nozzle holding tool 100 in a state facing up. Note that, the axis line of suction nozzle 60 held by nozzle holding tool 100 approximately matches the center of circular side illumination 102 in the vertical direction. Also, front illumination 104 is provided below first reflector 82 in a state facing up. Accordingly, side illumination 102 emits lights from below towards suction nozzle suction 60 held by nozzle holding tool 100, and front illumination 104 emits light from below towards suction nozzle suction 60 held by nozzle holding tool 100 via first reflector 82 and the internal section of side illumination 102.

Figure 5:
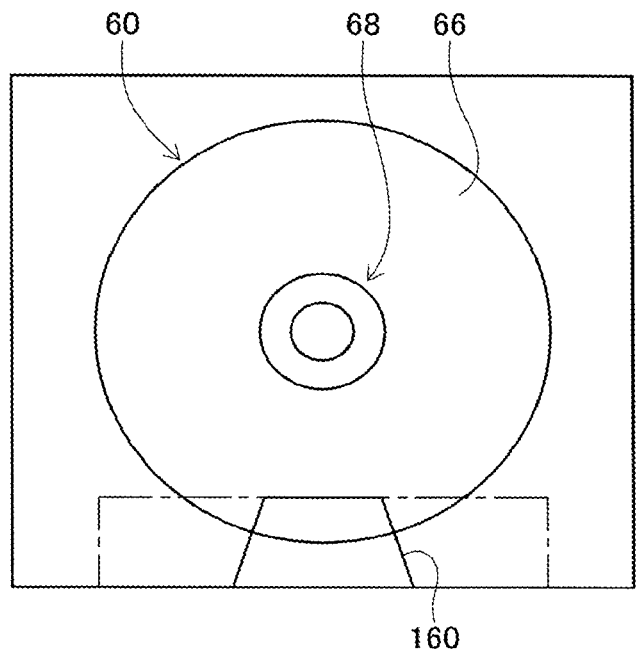
FIG. 5 shows an image of the bottom surface of a suction nozzle captured by the imaging device of the present disclosure.

Light emitted from side illumination 102 and front illumination 104, that is, light emitted from lower lighting device 88, is reflected by suction nozzle 60 held by nozzle holding tool 100, or by the reverse surface of side illumination 102, and hits first reflector 82 along a light path (the path between the two dotted lines 106). Then, 50% of the light that hit first reflector 82 is reflected by first reflector 82 and hits second reflector 84 along a light path (the path between the two dotted lines 108). This is because the reflectance of first reflector 82 is 50%. Camera 96 is provided along an extended path of the light that hits second reflector 84. Thus, 70% of the light that hit second reflector 84 passes through second reflector 84 and hits camera 96 along a light path (the path between the two dotted lines 110). Note that, camera 96 has lens 112 and imaging element 114, and light that hits camera 96 is detected by imaging element 114 via lens 112. By this, as shown in FIG. 5, image data of the lower surface of suction nozzle 60 is obtained. Note that, light detected by imaging element 114 is light corresponding to the light amount of 35% (0.5×0.7=0.35) of the light reflected from suction nozzle 60 held by nozzle holding tool 100 or the reverse surface of side illumination 102.

Further, side lighting device 90 of imaging device 80 is a backlight-type illumination device, and as shown in FIG. 4, is provided so as to emit light onto suction nozzle 60 held by nozzle holding tool 100, such that that light hits third reflector 86. Among the two light-blocking blocks 92 and 94, first light-blocking block 92 is provided between side light device 90 and suction nozzle 60 held by nozzle holding device 100, and second light-blocking block 94 is provided between third reflector 86 and suction nozzle 60 held by nozzle holding device 100. Slits 120 and 122 are formed respectively in first light-blocking block 92 and second light-blocking block 94, and those slits 120 and 122 match the direction of the light emitted from side lighting device 90. Thus, side lighting device 90 emits light onto suction nozzle 60 held by nozzle holding tool 100 between slit 120 of first light-blocking block 92; that emitted light hits third reflector 86 through slit 122 of second light-blocking block 94. Here, light emitted from side lighting device 90 hits third reflector 86 along a light path (the path between the two dotted lines 124).

Figure 6:
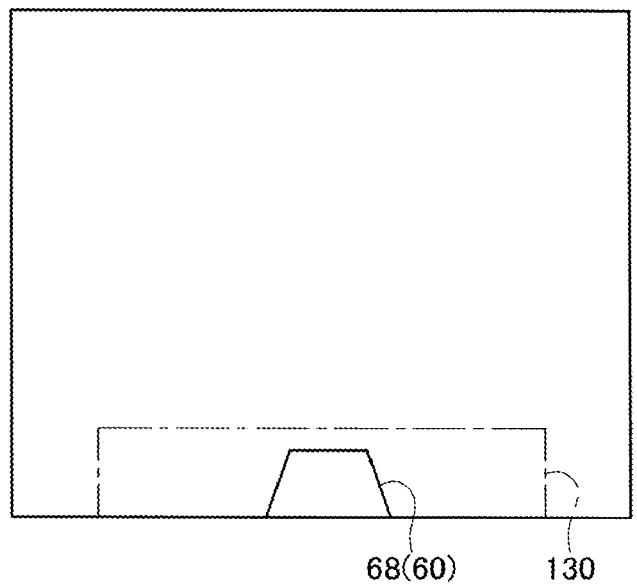
FIG. 6 shows an image of a side surface of a suction nozzle captured by the imaging device of the present disclosure.

Then, 100% of the light that hit third reflector 86 is reflected by third reflector 86 and hits second reflector 84 along a light path (the path between the two dotted lines 126). This is because the reflectance of third reflector 86 is 100%. Next, 30% of the light that hit second reflector 84 is reflected by second reflector 84 and hits camera 96 along a light path (the path between the two dotted lines 128). By this, as shown in FIG. 6, image data of suction nozzle 60 from the side is obtained. Note that, because light hitting camera 96 is light that passed through slit 122, the shape corresponds to slits 122, as shown by single-dashed line 130 in the figure. Also, light detected by imaging element 114 is light corresponding to the light amount of 30% (1.0× 0.3=0.3) of the light emitted from side lighting device 90.

As above, with imaging device 80, the lower surface of suction nozzle 60 is imaged by light hitting camera 96 via a first light path, specifically, the path between the two dotted lines 106, the path between the two dotted lines 108, and the path between the two dotted lines 110; and suction nozzle 60 is imaged from the side by light hitting camera 96 via a second light path, specifically, the path between the two dotted lines 124, the path between the two dotted lines 126, and the path between the two dotted lines 128. Accordingly, an imaging device is provided at low cost without needing to use two cameras, one for imaging the lower surface of suction nozzle suction 60, and one for imaging suction nozzle 60 from the side. Imaging suction nozzle 60 from two directions with one camera 96 using a first light path and a second light path depends on using the two light-blocking blocks 92 and 94. If these light-blocking blocks 92 and 94 did not exist, an image of suction nozzle 60 from the side would appear as a ghost image in the image of the lower surface of suction nozzle 60.

Figure 7:
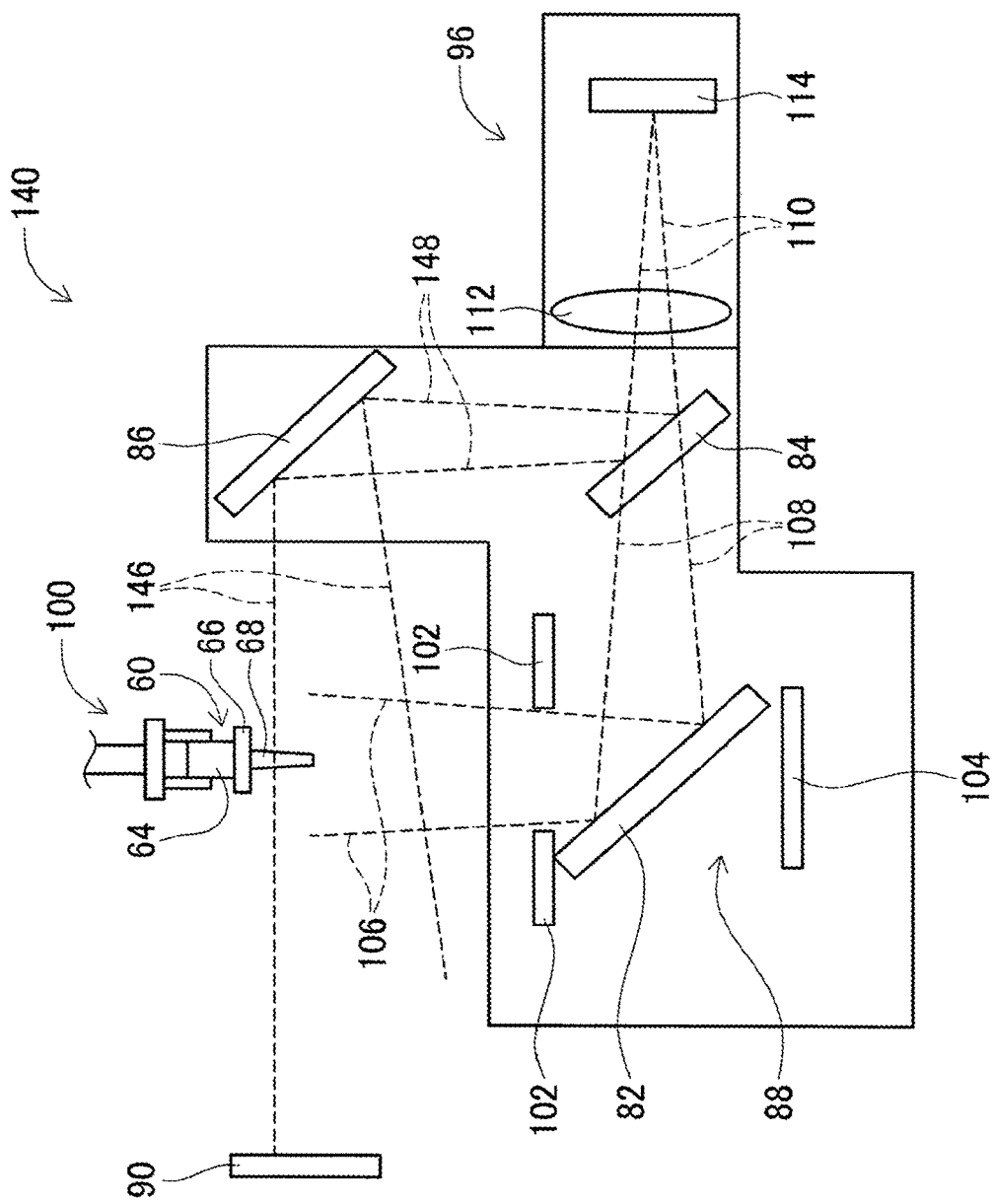
FIG. 7 is a schematic drawing showing a comparative example of an imaging device.

Specifically, an example of imaging device 140 that is not provided with light-blocking blocks 92 and 94 is described below with reference to FIG. 7. Except for the fact that light-blocking blocks 92 and 94 are not provided, imaging device 140 is the same as imaging device 80, thus, when describing imaging device 140, the same reference symbols are used for other configuration elements as with imaging device 80.

With imaging device 140, it is necessary to image the lower surface of suction nozzle 60, and when light is emitted by lower lighting device 88, that light, similar to imaging device 80, hits camera 96 via a first light path, that is, the path between the two dotted lines 106, the path between the two dotted lines 108, and the path between the two dotted lines 110. Also, light emitted from lower lighting device 88, in particular, light emitted from side illumination 102, may hit third reflector 86 directly, or be reflected by a scattering plate (not shown) of side lighting device 90. In such a case, light reflected from lower lighting device 88, when hitting third reflector 86 along a light path (the path between the two dotted lines 146) is reflected by third reflector 86. Then, light reflected by third reflector 86 hits second reflector 84 along a light path (the path between the two dotted lines 148). This light that hits second reflector 84, when reflected by second reflector 84, hits camera 96 along a light path (the path between the two dotted lines 110). This path (the path between the two dotted lines 110) is the same as the first light path, that is, the same as the light path for forming an image of the lower surface of suction nozzle 60. Therefore, imaging sensor 114 detects light for forming an image of the lower surface of suction nozzle 60 and light for forming an image of suction nozzle 60 from the side overlapping each other. Thus, an image of suction nozzle 60 from the side appears as a ghost image in the image of the lower surface of suction nozzle 60.

Figure 8:
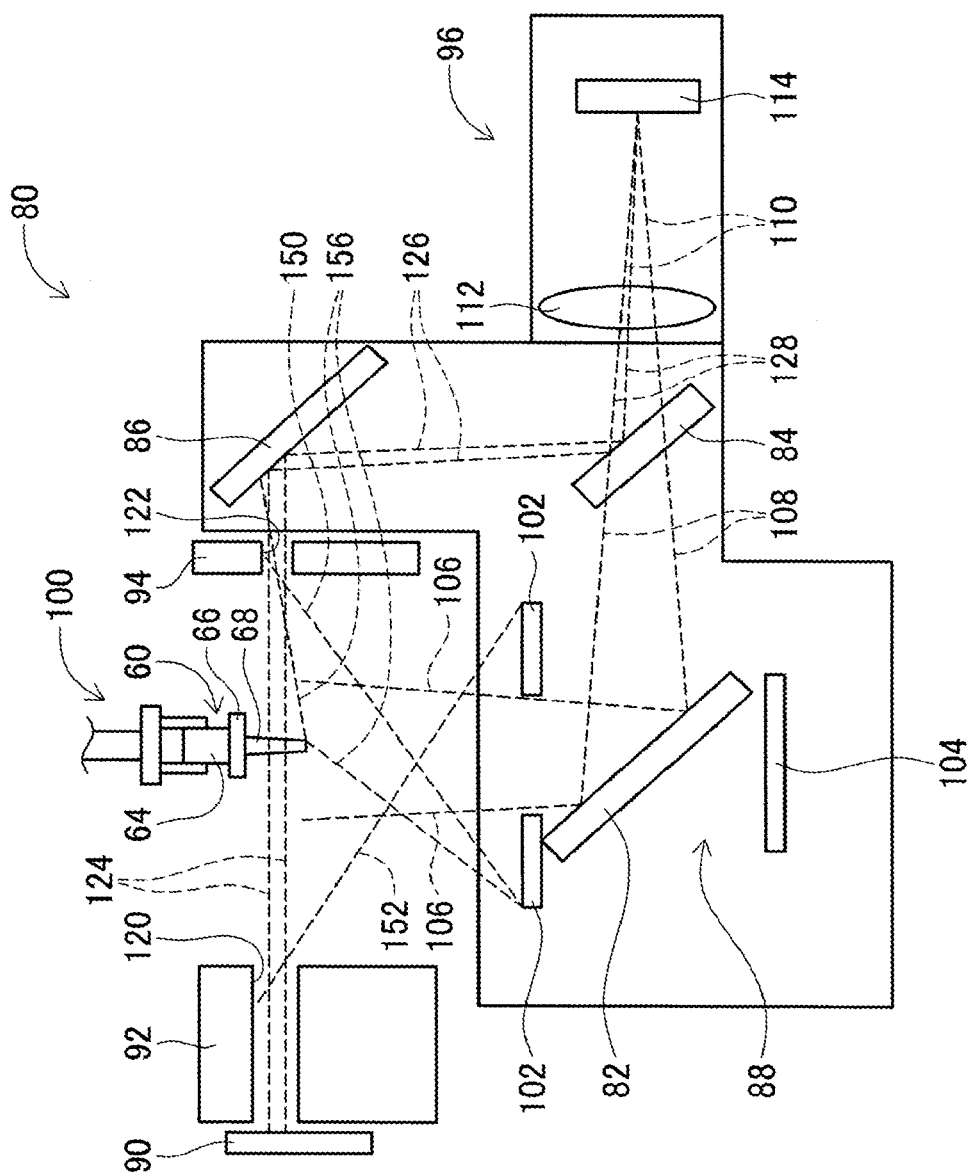
FIG. 8 is a schematic drawing showing an imaging device of the present disclosure.

Conversely, with imaging device 80, light-blocking blocks 92 and 94 block light emitted from lower lighting device 88, such that the appearance of a ghost image is prevented. Specifically, as shown in FIG. 8, even in a case in which light is emitted by side illumination 102 along the path shown by dotted lines 150, that light reaches inside slit 122 of second light-blocking block 94, but due to the thickness of second light-blocking block, is prevented from hitting third reflector 86. Also, even in a case in which light is emitted by side illumination 102 along the path shown by dotted line 152, that light reaches the inside of slit 120 of first light-blocking block, but due to the thickness of first light-blocking block 92, is prevented from hitting the scattering plate of side lighting device 90. That is, light is prevented from hitting third reflector 86 due to the reflecting of the light scattering plate of side lighting device 90. In this way, with imaging device 80, by blocking light emitted from lower lighting device 88 using light-blocking blocks 92 and 94, the appearance of a ghost image in the image of the lower surface of suction nozzle 60 is prevented.

However, light emitted from lower lighting device 88 is reflected by suction nozzle 60, and that reflected light may hit third reflector 86 via a light path along dotted line 156. Considering this, with imaging device 80, side lighting device 90 has light-blocking blocks 92 and 94 formed with slits 120 and 122, such that, when imaging the lower surface of suction nozzle 60, light hits the area around central portion of nozzle tube 68, not the lower end of suction nozzle 60, that is, the tip section of nozzle tube 68.

Figure 9:
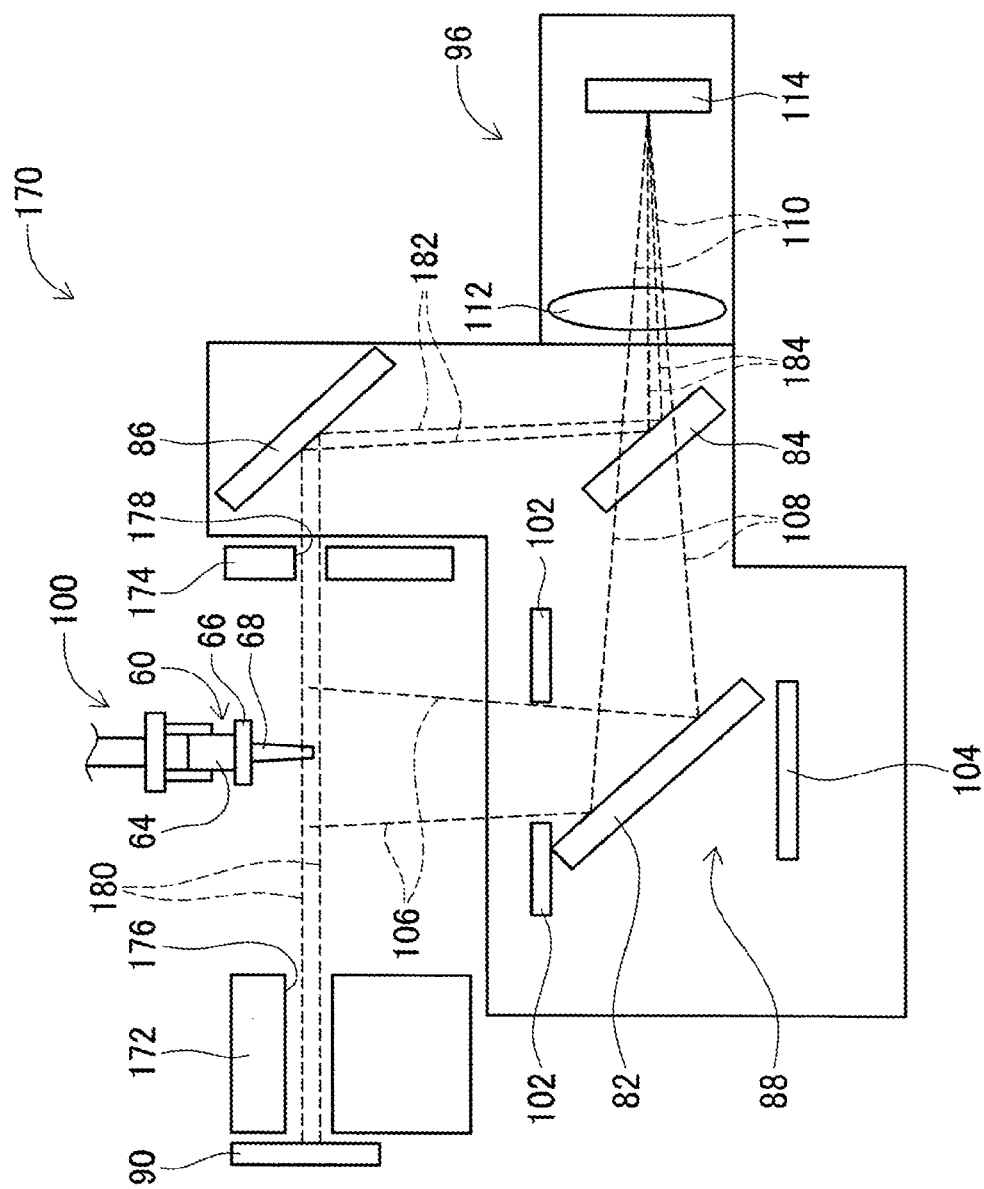
FIG. 9 is a schematic drawing showing a comparative example of an imaging device.

Specifically, for example, with imaging device 170 shown in FIG. 9, side lighting device 90 has light-blocking blocks 172 and 174 formed with slits 176 and 178 such that light hits the lower end of suction tube 68 of suction nozzle 60. Note that, except for light-blocking blocks 172 and 174, imaging device 170 is the same as imaging device 80, thus, when describing imaging device 170, the same reference symbols are used for other configuration elements as with imaging device 80.

Figure 10:
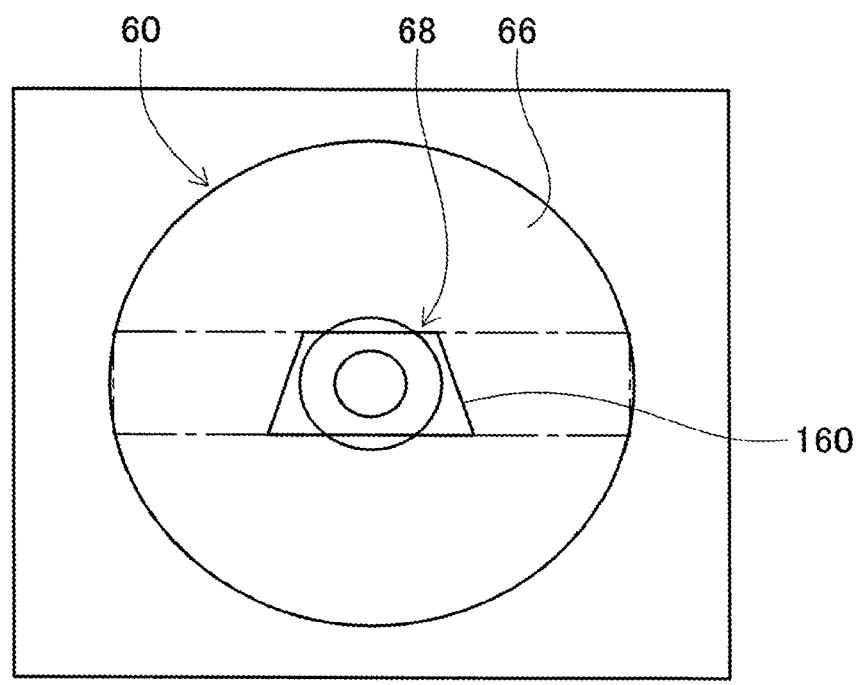
FIG. 10 shows an image of the bottom surface of a suction nozzle captured by the comparative example of an imaging device.

With imaging device 170, light emitted from lower lighting device 88 is reflected by suction nozzle 60, and that reflected light may hit third reflector 86 between slit 178 of light-blocking block 174. In this case, light reflected by suction nozzle 60 hits third reflector 86 along a light path (the path between the two dotted lines 180). Then, this light that hits third reflector 86 is reflected by third reflector 86 and hits second reflector 84 along a light path (the path between the two dotted lines 182). This light that hits second reflector 84, when reflected by second reflector 84, hits camera 96 along a light path (the path between the two dotted lines 184). The path of the light that hits camera 96 is the path between the two dotted lines 184, and is positioned in a central portion of the light path for forming an image of the lower surface of suction nozzle 60 (the path between the two dotted lines 110). Thus, as shown in FIG. 10, due to light hitting camera 96 via the path between the two dotted lines 184, a ghost image, as shown by solid line 160, may appear in a central portion of the image of the lower surface of suction nozzle 60. In this way, because a ghost image appears in a central portion of the image of the lower surface of suction nozzle 60, inspection of the lower surface of suction nozzle 60 is hindered, and it is not possible to appropriately inspect the state of the lower side of suction nozzle 60, that is, the state of suction tube 68 of suction nozzle 60.

Conversely, with imaging device 80, as shown in FIG. 8, side lighting device 90 has light-blocking blocks 92 and 94 formed with slits 120 and 122, such that, when imaging the lower surface of suction nozzle 60, light hits the area around central portion of nozzle tube 68 of suction nozzle 60. Thus, when light reflected by suction nozzle 60 hits third reflector 86, as given above, that light hits camera 96 via the second light path, that is, the path between the two dotted lines 124, the path between the two dotted lines 126, and the path between the two dotted lines 128. The path of the light that hits camera 96 is the path between the two dotted lines 128, and is positioned at an edge of the light path for forming an image of the lower surface of suction nozzle 60 (the path between the two dotted lines 110). Thus, as shown in FIG. 5, although a ghost image as shown by solid line 160 appears in the image of the lower surface of suction nozzle 60 due to light hitting camera 96 via the path between the two dotted lines 128, this ghost image appears in a different position to the image of the lower surface of suction nozzle 60, and therefore does not hinder inspection of the lower surface of suction nozzle 60. By this, it is possible to appropriately inspect the state of suction tube 68 of suction nozzle 60.

In this way, with imaging device 80, as well as by providing reflectors 84 and 86 and light-blocking blocks 92 and 94, by arranging those reflectors 84 and 86 in appropriate positions and by forming slits 120 and 122 in light-blocking blocks 92 and 94 at appropriate positions, it is possible to appropriately image the lower surface of suction nozzle 60 and thus to appropriately inspect the state of suction tube 68 of suction nozzle 60.

Also, the purpose of imaging suction nozzle 60 from the side is to inspect the protrusion amount of suction tube 68 from body pipe 64, thus imaging the tip section of suction tube 68 is necessary. That is, the position of the tip of suction tube 68 is detected based on the image data, and the protrusion amount of suction tube 68 from body pipe 64 is calculated based on the position of the tip of suction tube 68. However, with imaging device 80, as described above, side lighting device 90 has light-blocking blocks 92 and 94 formed with slits 120 and 122, such that, when imaging the lower surface of suction nozzle 60, light hits the area around central portion of nozzle tube 68 of suction nozzle 60. That is, when imaging suction nozzle 60 from the side at the position at which the lower surface of suction nozzle 60 is imaged, because the central portion of suction tube 68 of suction nozzle 60 is imaged, it is not possible to calculate the protrusion amount of suction tube 68 from body pipe 64. Due to this, when imaging suction nozzle 60 from the side, suction nozzle 60 is moved such that light hits the tip section of suction tube 68 of suction nozzle 60 from side lighting device 90.

Figure 11:
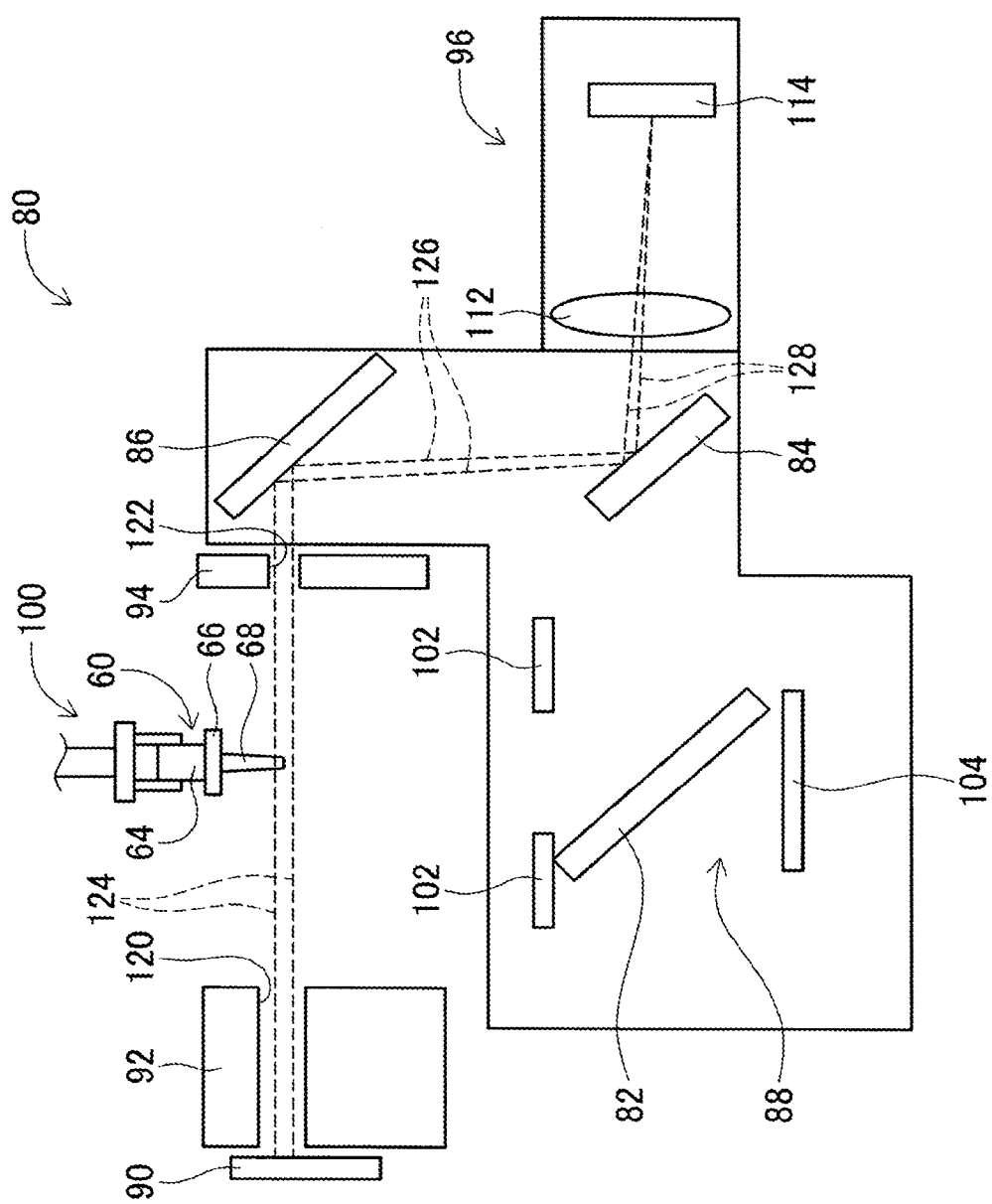
FIG. 11 is a schematic drawing showing an imaging device of the present disclosure.

Specifically, when imaging suction nozzle 60 from the side, as shown in FIG. 11, nozzle holding tool 100 is moved up such that the tip section of suction pipe 68 of suction nozzle 60 is positioned on the path of light emitted from side lighting device 90 (the path between the two dotted lines 124). By this, light emitted from side lighting device 90 hits camera 96 via the second path, that is, the path between the two dotted lines 124, the path between the two dotted lines 126, and the path between the two dotted lines 128, such that, as shown in FIG. 6, the tip section of suction tube 68 of suction nozzle 60 is imaged.

In this way, with imaging device 80, by arranging light-blocking blocks 92 and 94, and forming slits 120 and 122, in appropriate positions, and changing the imaging position based on the imaging location of suction nozzle 60, and the like, it is possible to appropriately image the lower surface of suction nozzle 60 and the side of suction nozzle 60 using a single camera 96.

Also, with imaging device 80, the distance via the first light path between suction nozzle 60 and camera 96 when imaging the lower surface of suction nozzle 60, and the distance via the second light path between suction nozzle 60 and camera 96 when imaging suction nozzle 60 from the side are the same. That is, the distance between suction nozzle 60 and camera 96 via the path between the two dotted lines 106, the path between the two dotted lines 108, and the path between the two dotted lines 110 shown in FIG. 4; and the distance between suction nozzle 60 and camera 96 via the path between the two dotted lines 124, the path between the two dotted lines 126, and the path between the two dotted lines 128 shown in FIG. 11, are the same. By this, adjusting the focus is not necessary when imaging the lower surface of suction nozzle 60 or when imaging suction nozzle 60 from the side, meaning that the imaging device has extremely good usability.

Note that, in the above embodiment, suction nozzle 60 is an example of a suction nozzle. Imaging device 80 is an example of a detection device. Lower lighting device 88 is an example of a first light source. Side lighting device 90 is an example of a second light source. First reflector 82 and second reflector 84 are each an example of a first light-guiding member. Second reflector 84 and third reflector 86 are each an example of a second light-guiding member. Light-blocking blocks 92 and 94 are each an example of a light-blocking block.

Further, the present disclosure is not limited to the above example embodiments, and various changed or improved methods of embodiment are possible based on the knowledge of someone skilled in the art. Specifically, for example, in the present embodiment, as a member for blocking light, light-blocking blocks 92 and 94 are used; however, various forms of light-blocking members may be used, so long as they have a form that blocks light. Also, slits 120 and 122 are formed in light-blocking blocks 92 and 94, with light passing between those slits 120 and 122; however, various types of hole sections may be used, so long as light is able to pass through the light-blocking member. Specifically, for example, a light-blocking member with a configuration such that light passes through a U-shaped recess formed by the edges, with light being blocked at other locations except the recess, may be used.

Also, in the present embodiment, the present disclosure of a detection device is used for imaging a suction nozzle; however, the present disclosure of a detection device may be used for imaging various other members other than a suction nozzle.

Also, in the present disclosure, slits 120 and 122 are formed such that the position for imaging suction nozzle 60 from the side is above the position for imaging the lower surface of suction nozzle 60; however, slits 120 and 122 may be formed at positions such that the position for imaging suction nozzle 60 from the side and the position for imaging the lower surface of suction nozzle 60 are different. That is, slits 120 and 122 may be formed such that the position for imaging suction nozzle 60 from the side is below the position for imaging the lower surface of suction nozzle 60.

Also, the purpose of imaging suction nozzle 60 from the side may be to inspect foreign matter on the tip of a suction nozzle, or to inspect whether a component is attached to the tip of a suction nozzle.

REFERENCE SIGNS LIST

60: suction nozzle; 80: imaging device (detection device); 88: lower lighting device (first light source); 90: side lighting device (second light source); 82: reflector (first light-guiding member); 84: reflector (first light-guiding member), (second light-guiding member); 86: reflector (second light-guiding member); 92: light-blocking block (light-blocking member); 94: light-blocking block (light-blocking member)

The invention claimed is:

1. A detection device that detects light emitted onto a detection target object, the detection device comprising:
    a first light source that emits light onto the detection target object from a first direction;
    a second light source that emits light onto the detection target object from a second direction;
    a detecting section for detecting light emitted from the first light source and light emitted from the second light source;
    a first guiding member that guides light emitted from the first light source to the detecting section via a first light path;
    a second guiding member that guides light emitted from the second light source to the detecting section via a second light path; and
    a light-blocking member that applies an aperture to the light emitted from the first light source restricting the first light path such that the first light path does not overlap the second light path and the light emitted from the first light source does not arrive at the detecting section along the second light path.

2. The detection device according to claim 1, wherein
    the detection target object is arranged at a first position when light emitted from the first light source is detected by the detecting section; and
    the detection target object is arranged at a second position when light emitted from the second light source is detected by the detecting section.

3. The detection device according to claim 2, wherein
    the distance between the first position and the detecting section via the first light path, and the distance between the second position and the detecting section via the second light path, are the same.

4. The detection device according to claim 1, wherein
    the detection device is a device for imaging a suction nozzle as a detection target object based on light detected by the detecting section, the detection device imaging a lower surface of the suction nozzle and a side surface of the suction nozzle by the first light source emitting light from below the suction nozzle, and the second light source emitting light from sideways of the suction nozzle.

5. The detection device according to claim 1, wherein the light-blocking member is provided between the second light source and the detection target.

6. The detection device according to claim 1, further comprising:
    another light-blocking member, wherein
    the light-blocking member is provided between the second light source and the detection target and the another light-blocking member is provided between the detection target and the detection device.

* * * * *